(12) United States Patent
Bui et al.

(10) Patent No.: US 8,597,621 B2
(45) Date of Patent: *Dec. 3, 2013

(54) SHINE-IMPARTING HYDRATING AND MOISTURIZING EMULSION LIPSTICK COMPOSITION

(75) Inventors: Hy Si Bui, Piscataway, NJ (US); Mohamed Kanji, Edison, NJ (US); Liana Esposito, Westfield, NJ (US)

(73) Assignee: L'oreal, Paris (FR)

(*) Notice: Subject to any disclaimer, the term of this patent is extended or adjusted under 35 U.S.C. 154(b) by 198 days.

This patent is subject to a terminal disclaimer.

(21) Appl. No.: 13/129,543

(22) PCT Filed: Dec. 16, 2009

(86) PCT No.: PCT/US2009/006579
§ 371 (c)(1),
(2), (4) Date: May 16, 2011

(87) PCT Pub. No.: WO2010/074726
PCT Pub. Date: Jul. 1, 2010

(65) Prior Publication Data
US 2011/0223122 A1    Sep. 15, 2011

Related U.S. Application Data

(60) Provisional application No. 61/122,838, filed on Dec. 16, 2008.

(51) Int. Cl.
*A61K 8/06* (2006.01)
*A61K 8/92* (2006.01)

(52) U.S. Cl.
USPC .................... 424/64; 424/401; 424/486

(58) Field of Classification Search
None
See application file for complete search history.

(56) References Cited

U.S. PATENT DOCUMENTS

| | | | |
|---|---|---|---|
| 2,957,838 A | 10/1960 | Mills, Jr. | |
| 4,226,889 A | 10/1980 | Yuhas | |
| 4,871,536 A | 10/1989 | Arraudeau et al. | |
| 5,032,391 A | 7/1991 | Helioff et al. | |
| 5,618,524 A | 4/1997 | Bolich, Jr. et al. | |
| 5,998,547 A | 12/1999 | Hohner | |
| 6,482,400 B1 | 11/2002 | Collin | |
| 6,492,455 B1 | 12/2002 | Nadolsky | |
| 6,524,564 B1 | 2/2003 | Kim et al. | |
| 7,682,621 B2 | 3/2010 | Lamberty et al. | |
| 2004/0223986 A9 | 11/2004 | Boussouira et al. | |
| 2005/0013992 A1 | 1/2005 | Azad et al. | |
| 2006/0159642 A1 | 7/2006 | Hanna et al. | |
| 2006/0188459 A1* | 8/2006 | Heinrichs et al. | 424/63 |
| 2007/0031361 A1 | 2/2007 | Herrmann et al. | |
| 2007/0110700 A1 | 5/2007 | Wells et al. | |
| 2007/0110702 A1 | 5/2007 | Ehara | |
| 2007/0259012 A1 | 11/2007 | Castro et al. | |
| 2008/0207871 A1 | 8/2008 | Seiler et al. | |
| 2010/0330012 A1 | 12/2010 | Bui et al. | |
| 2010/0330015 A1 | 12/2010 | Bui et al. | |
| 2010/0330016 A1 | 12/2010 | Bui et al. | |
| 2010/0330017 A1 | 12/2010 | Bui et al. | |
| 2010/0330022 A1 | 12/2010 | Bui et al. | |
| 2010/0330024 A1 | 12/2010 | Bui et al. | |
| 2011/0020254 A1 | 1/2011 | Bui et al. | |
| 2011/0020255 A1 | 1/2011 | Bui et al. | |
| 2011/0020256 A1 | 1/2011 | Bui et al. | |
| 2011/0020257 A1 | 1/2011 | Bui et al. | |
| 2011/0020260 A1 | 1/2011 | Bui et al. | |
| 2011/0020261 A1 | 1/2011 | Bui et al. | |
| 2011/0021681 A1 | 1/2011 | Bui et al. | |
| 2011/0021683 A1 | 1/2011 | Bui et al. | |
| 2011/0038819 A1 | 2/2011 | Bui et al. | |
| 2011/0223123 A1 | 9/2011 | Bui et al. | |
| 2011/0280817 A1 | 11/2011 | Ramadan et al. | |
| 2011/0280818 A1 | 11/2011 | Kawaratani et al. | |
| 2011/0280820 A1 | 11/2011 | Bui et al. | |
| 2011/0286950 A1 | 11/2011 | Bui et al. | |
| 2011/0286951 A1 | 11/2011 | Bui et al. | |
| 2011/0293550 A1 | 12/2011 | Bui et al. | |
| 2011/0300088 A1* | 12/2011 | Bui et al. | 424/64 |
| 2011/0311467 A1 | 12/2011 | Bui et al. | |
| 2012/0004327 A1 | 1/2012 | Bui et al. | |
| 2012/0107263 A1 | 5/2012 | Bui et al. | |

FOREIGN PATENT DOCUMENTS

| | | |
|---|---|---|
| DE | 100 64 799 | 6/2002 |
| DE | 103004008941 | 9/2005 |
| EP | 2 036 536 | 3/2009 |
| WO | WO 96/03967 | 2/1996 |
| WO | WO 01/17485 | 3/2001 |
| WO | WO 02/088456 A1 | 11/2002 |
| WO | WO 2006/112690 | 10/2006 |
| WO | WO 2006/127883 | 11/2006 |
| WO | WO 2007/048672 | 5/2007 |
| WO | WO 2007/096400 | 8/2007 |
| WO | WO 2007/139812 | 12/2007 |
| WO | WO 2008/046763 | 4/2008 |
| WO | WO 2009/085888 | 7/2009 |

OTHER PUBLICATIONS

International Search Report issued Jul. 27, 2010 in PCT/US09/006579 filed Dec. 16, 2009.
Bergbreiter et al., Tit. Lett., 1997, 38 (21), 3703-3706.
L. Rudnick, Synthesis, Mineral Oils, and Bio-Based Lubricants, Chemistry and Technology, 2006.
http://www.Chemical Book.com/ChemicalProductProperty_EN_CB3748204.htm, Poly(methyl vinyl ether-alt-maleic anhydride), 2010.

* cited by examiner

*Primary Examiner* — Ernst Arnold
(74) *Attorney, Agent, or Firm* — Oblon, Spivak, McClelland, Maier & Neustadt, L.L.P.

(57) ABSTRACT

The present invention is directed to emulsion composition, in solid form, capable of imparting shine, hydration and/or moisturization onto lips containing: a) at least one polyamine; (b) at least one oil-soluble high carbon polar modified polymer; (c) water; (d) at least one non-volatile solvent; (e) at least one wax having a high melting point; and (e) optionally, at least one colorant.

21 Claims, No Drawings

US 8,597,621 B2

SHINE-IMPARTING HYDRATING AND MOISTURIZING EMULSION LIPSTICK COMPOSITION

FIELD OF THE INVENTION

The present invention generally relates to a novel hydrating, moisturizing and shine-imparting lipstick composition. More particularly, the present invention relates to a shine-imparting emulsion lipstick composition, in stick form, capable of hydrating and moisturizing the lips due to the presence of a significant amount of stabilized water and oil contained therein.

DISCUSSION OF THE BACKGROUND

The problem with conventional solid lipsticks which claim to hydrate and moisturize the lips is that only a small amount of water is typically incorporated therein which tends to evaporate very quickly yielding little, to no, hydrating and moisturizing effect. The addition of more water typically results in poor stick structure and payoff. Moreover, these types of conventional hydrating and moisturizing lipsticks require the use of surfactants in order to form the emulsion.

Also, conventional lipstick compositions which impart a high degree of shine/gloss onto the lip surface typically require the use of silicone fluids in the composition. Silicone fluids are known to have high refractive indices which provide shine. These types of silicone fluids, however, have poor environmental profiles and, because they are relatively expensive, add to the cost of goods.

Therefore, it is an object of the present invention to provide a lipstick composition, which imparts a high degree of shine, while at the same time both hydrating and moisturizing the lips in a continuous manner, even in the absence of silicone fluids.

Another objective of the present invention is to provide a solid lipstick composition containing a significant amount of water, in a stable emulsion, without having to use an emulsifier to form the emulsion.

BRIEF SUMMARY OF THE INVENTION

The present invention relates to a stable emulsion lip composition, in solid form, comprising:
(a) at least one oil-soluble high carbon polar modified polymer;
(b) at least one polyamine;
(c) water;
(d) at least one non-volatile solvent capable of solubilizing the oil-soluble high carbon polar modified polymer;
(e) at least one wax; and
(f) optionally, at least one colorant.

The present invention also relates to a stable emulsion lip composition, in solid form, comprising:
(a) a reaction product of at least one oil-soluble high carbon polar modified polymer and at least one polyamine;
(b) water;
(c) at least one non-volatile solvent capable of solubilizing the oil-soluble high carbon polar modified polymer;
(d) at least one wax; and
(e) optionally, at least one colorant.

The present invention relates to a stable emulsion lip composition, in solid form, made by combining ingredients comprising:
(a) at least one oil-soluble high carbon polar modified polymer;
(b) at least one polyamine;
(b) water;
(c) at least one non-volatile solvent capable of solubilizing the oil-soluble high carbon polar modified polymer;
(d) at least one wax; and
(e) optionally, at least one colorant.

Preferably, the composition does not require or contain an emulsifier in order to form the emulsion or silicone fluids in order to deliver shine.

The present invention also relates to methods of imparting shine, hydration and/or moisturization onto lips by applying the above-disclosed compositions onto the lips.

It has been surprisingly discovered that the resultant composition, even with the presence of water therein, is stable in the absence of emulsifiers, has good stick hardness, delivers hydration and moisture onto the lips in a comfortable manner, is easily deposited onto the lips and imparts a high degree of shine without the need for silicone fluids.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C.

"Non-volatile", as used herein, means having a flash point of greater than about 100° C.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

Polyamine Compound

According to the present invention, compositions comprising at least one polyamine compound are provided. In accordance with the present invention, the polyamine compound has at least two primary amine groups available to react with hydrophilic groups of the oil-soluble polar modified polymer.

According to particularly preferred embodiments, the polyamine compound is a polyalkyleneimine, preferably a C2-C5 polyalkyleneamine compound, more preferably a polyethyleneimine or polypropyleneimine. Most preferably, the polyalkylenamine is polyethyleneimine ("PEI"). The polyalkyleneamine compound preferably has an average molecular weight range of from 500-200,000, including all ranges and subranges therebetween.

According to preferred embodiments, compositions of the present invention contain polyethyleneimine compounds in the form of branched polymers. Commercially available examples of such polymers are available from BASF under the tradename LUPASOL or POLYIMIN. Non-limiting examples of such polyethyleneimines include Lupasol® PS, Lupasol® PL, Lupasol® PR8515, Lupasol® G20, Lupasol® G35.

According to other embodiments of the present invention, polyamines such as polyethyleneimines and polypropyleneimines can be in the form of dendrimers. Non-limiting examples of such dendrimers are manufactured by the company DSM, and/or are disclosed in U.S. Pat. No. 5,530,092 and U.S. Pat. No. 5,610,268, the contents of which are hereby incorporated by reference. Commercially available examples of such polymers include polyamidoamine or polypropyleneimine polymers from DENDRITECH sold under the STARBURST® name.

According to other embodiments of the present invention, derivatives of polyalkyleneamines are suitable polyamines. Such derivatives include, but are not limited to, alkylated derivatives, the addition products of alkylcarboxylic acids to polyalkyleneamines, the addition products of ketones and of aldehydes to polyalkyleneamines, the addition products of isocyanates and of isothiocyanates to polyalkyleneamines, the addition products of alkylene oxide or of polyalkylene oxide block polymers to polyalkyleneamines, quaternized derivatives of polyalkyleneamines, the addition products of a silicone to polyalkyleneamines, and copolymers of dicarboxylic acid and polyalkyleneamines. Even further suitable polymamines include, but are not limited to, polyvinylimidazoles (homopolymers or copolymers), polyvinylpyridines (homopolymers or copolymers), compounds comprising vinylimidazole monomers (see, for example, U.S. Pat. No. 5,677,384, hereby incorporated by reference), and polymers based on amino acids containing a basic side chain (preferably selected from proteins and peptides comprising at least 5%, preferably at least 10% of amino acids selected from histidine, lysine and arginine). Such suitable polyamines as described above include those disclosed and described in U.S. Pat. No. 6,162,448, the contents of which are hereby incorporated by reference. Commercially available examples of such polymers include polyvinylamine/formamide such as those sold under the Lupamine® name by BASF, chitosan from vegetable origin such as those sold under the Kiosmetine® or Kitozyme® names, or copolymer 845 sold by ISP.

According to preferred embodiments, the at least one polyamine compound is present in the composition of the present invention in an amount ranging from about 0.05 to about 5% by weight, more preferably from about 0.1 to about 2% by weight, more preferably from about 0.125 to about 1% based on the total weight of the composition, including all ranges and subranges within these ranges.

Preferably, the amount of polyamine compound reacted with the oil-soluble polar modified polymer is such that at least two amine groups on the polyamine compound react with the oil-soluble polar modified polymer to form links or bonds between the amine groups and the hydrophilic groups of the oil-soluble polar modified polymer. The appropriate amount of polyamine compound to react with the oil-soluble polar modified polymer to obtain a reaction product can be easily determined, taking into account the number/amount of reactive amine groups on the polyamine compound and the number/amount of corresponding reactive groups on the oil-soluble polar modified polymer (for example, maleic anhydride groups). According to preferred embodiments, excess oil-soluble polar modified polymer (as determined by the relative number/amount of corresponding reactive groups on the polymer as compared to the reactive amine groups on the polyamine) is reacted with polyamine. Preferably, the polyamine to oil-soluble polar modified ratio is between 0.005 and 1, preferably between 0.006 and 0.5, and preferably between 0.007 and 0.1, including all ranges and subranges therebetween.

Oil-Soluble High Carbon Polar Modified Polymer

According to the present invention, compositions comprising at least one oil-soluble high carbon polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30000 g/mol, preferably of 500 to 10000 g/mol and particularly preferably of 1000 to 5,000 g/mol, including all ranges and subranges therebetween;

a number-average molecular weight Mn of less than or equal to 15000 g/mol, preferably of 500 to 12000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the hompopolymers and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the LicoCare name having designations such as CM 401, which is a maleic anhydride modified wax having a Mw of 2025 and a crystallinity of 11%, C30-C38 olefin/isopropylmaleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

Preferably, the oil-soluble high carbon polar modified polymer(s) represent from about 3% to about 20% of the total weight of the composition, more preferably from about 4% to about 15% of the total weight of the composition, and most preferably from about 5% to about 10%, including all ranges and subranges therebetween.

Reaction Product

According to preferred embodiments of the present invention, the oil-soluble high carbon polar modified polymer is reacted with the polyamine compound, in the presence of water in, at minimum, an amount sufficient to solubilize the polyamine, to form a reaction product. In accordance with the preferred embodiments, the reaction product is water-insoluble.

Although not wanting to be bound by any particular theory, it is believed that at a temperature below 100° C., the reaction of the oil-soluble high carbon polar modified polymer with the primary amine group of the polyamine opens the anhydride ring to form a half acid and half amide crosslinked product. However, at a temperature above 100° C., the reaction of the oil-soluble polar modified polymer with the primary amine group of the polyamine opens the anhydride ring to form an imide crosslinked product. The former product is preferred over the latter product. It is not necessary for all amine groups and all hydrophilic groups to react with each other to form the reaction product. Rather, it is possible that the composition may contain free polyamine and/or free oil-soluble polar modified polymer in addition to the reaction product.

Although not wanting to be bound by any particular theory, it is also believed that the polyamine(s) can be non-covalently assembled with the high carbon polar modified polymer(s) by electrostatic interaction between an amine group of the polyamine and a hydrophilic group (for example, carboxylic acid group associated with maleic anhydride groups) of the high carbon polar modified polymer to form a supramolecule. For example, with specific reference to maleic anhydride groups, in the presence of water these groups can open to form dicarboxylic acid groups which can interact with protonated primary amines of the polyamine through ionic interaction to form a polymer-polymer complex with hydrophilic core crosslinkers and a hydrophobic network that act as supramolecular capsule. If a large amount of maleic anhydride groups are present, the secondary amine groups of polyamine are also protonated and interact with alkyl carboxylates.

According to preferred embodiments, the oil-soluble high carbon polar modified polymer is in an oil carrier, and the polyamine compound is in an aqueous carrier, and the reaction occurs by combining the oil carrier and the aqueous carrier. Because the oil-soluble high carbon polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C.

Without intending to be bound by any particular theory, it is believed that the reason for this is that due to the chemical and physical reactions which take place when the oil-soluble high carbon polar modified polymer is combined with the polyamine, the subsequent reaction product that is formed is surprisingly and unexpectedly able to entrap large amounts of water molecules within its hydrophobic matrix. The resultant product is eminently capable of forming a film, is self-emulsifying, waterproof. Moreover, the product is both stable and capable of carrying various types of ingredients.

Non-Volatile Oil for Solubilizing the Oil-Soluble High Carbon Polar Modified Polymer The cosmetic compositions of the present invention comprise at least one non-volatile solvent capable of solubilizing the oil-soluble high carbon polar modified polymer. As used herein, the term "non-volatile" means having a boiling point of greater than about 100° C. The at least one non-volatile solvent preferably comprises at least one non-volatile oil.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula R5COOR6 in which R5 represents a linear or branched higher fatty acid residue containing from 1 to 40 carbon atoms, including from 7 to 19 carbon atoms, and R6 represents a branched hydrocarbon-based chain containing from 1 to 40 carbon atoms, including from 3 to 20 carbon atoms, with R6+R7☐10, such as, for example, Purcellin oil (cetostearyl octanoate), isononyl isononanoate, C12 to C15 alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

C8 to C26 fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

The at least one non-volatile solvent is preferably present in the composition of the invention in an amount of from about 20% to about 90% by weight, such as from about 30% to about 80% by weight, such as from about 40% to about 70% by weight, including all ranges and subranges therebetween, all weights being based on the total weight of the composition.

Water

The composition of the present invention also contains water. The water is entrapped within the composition in a stable manner so that it is capable of providing hydration and/or moisture to the lips.

The water is preferably present in an amount of from about 0.1% to about 50% by weight, such as from about 5% to about 40% by weight, such as from about 10% to about 35% by weight, including all ranges and subranges therebetween, all weights being based on the total weight of the composition.

Wax

The composition of present invention includes the presence of at least one wax having a high melting point that is compatible with the composition. As used herein, "high melting point wax" may be any lipophilic fatty compound having a melting point of 75° C. or higher. Non-limiting examples of suitable waxes include waxes of natural origin such as beeswax, carnauba wax, candelilla wax, ouricury wax, Japan wax, cork fiber wax, paraffin wax, microcrystalline wax, sugar cane wax, lignite wax, montan wax, hydrogenated oils, waxes of synthetic origin, and the like.

In general, the wax is preferably present in the composition in an amount of from about 5 to about 20% by weight, such as from about 6 to about 15% by weight, and from about 7 to about 10% by weight, including all ranges and subranges therebetween, all weights being based on the total weight of the composition.

Colorant

The composition of the present invention may also contain at least one colorant, such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the cosmetic compositions of the invention will depend on the color, intensity and use of the cosmetic composition and, as a result, will be determined by those skilled in the art of cosmetic formulation.

Optional Ingredients

The composition of the present invention may also include any one, or more, optional ingredients. Examples thereof include, but are not limited to, co-solvents (volatile and/or non-volatile), plasticizers, preservatives, fillers, active ingredients and sunscreens.

It has surprisingly been discovered that the composition of the present invention forms a stable emulsion, in solid form, without having to employ an emulsifier to form the emulsion.

It has also been surprisingly discovered that the composition is capable of imparting enhanced hydration and/or moisturization onto lips treated therewith. Without intending to be bound by theory, it is believed that the combination of the polyamine and oil-soluble high carbon polar modified polymer forms a matrix capable of entrapping the water and oil emulsion. Consequently, when the composition is applied onto the lips, the water, rather than immediately evaporating from the surface of the lips, thereby imparting no further hydration/moisturizing properties, instead remains within the matrix until it is released therefrom by the friction caused by a consumer when their lips come together during the normal course of the day. As a result, hydrating/moisturizing water is released onto the surface of the lips over a prolonged period of time.

It also has surprisingly been discovered that the composition of the present invention delivers a shine upon applied on the lips without having to employ silicone fluids.

The composition of the present invention preferably possesses a hardness value of from about 50 to about 200, such as from about 70 to about 150, and from about 80 to about 100 gram force.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is 50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

The present invention is further described in terms of the following non-limiting examples. Unless otherwise indicated, all parts and percentages are on a weight-by-weight percentage.

Examples 1-4

| Phase | INCI Name | Trade Name | Ex 1 | Ex 2 |
|-------|-----------|------------|------|------|
| A | Octododecanol | | 15.00 | 4.20 |
| A | Octyldodecyl neopentanoate | | 0.00 | 17.90 |
| A | Hydrogenated Polydecene | Puresyn 6 | 23.60 | 18.00 |
| A | Hydrogenated Polydecene | Puresyn 150 | 0.00 | 3.00 |
| A | C26-28 α-olefin-maleic acid anhydride copolymer wax | Licocare CM401 | 7.00 | 10.00 |
| A | VP/Eicosene copolymer | | 0.00 | 2.00 |
| A | Polyethylene | Performalene 500-L Polyethylene | 8.00 | 8.00 |
| A | Pigments | | 2.65 | 2.65 |
| A | Tricaprylin | | 6.70 | 6.70 |
| A | Pearl | | 4.30 | 4.30 |
| B | Deionized Water | | 22.50 | 20.00 |
| B | b-Polyethyleneimine (50% solid/50% water) | Lupasol G 35 | 0.25 | 0.25 |
| B | Glycerin | | 10.00 | 3.00 |
| | Total | | 100.00 | 100.00 |

The hardness of the sticks in examples 1 & 2 was determined to be 145 and 150 gram-force, respectively.

| Phase | INCI Name | Trade Name | Ex 3 | Ex 4 |
|-------|-----------|------------|------|------|
| A | Octododecanol | | 15.00 | 15 |
| A | Hydrogenated Polydecene | Puresyn 6 | 16.1 | 11.00 |
| A | C26-28 α-olefin-maleic acid anhydride copolymer wax | Licocare CM401 | 7.00 | 10.00 |
| A | Polyethylene | Performalene 400 | 8.00 | 2.14 |
| A | Polyethylene | Performalene 500 | 0.00 | 2.86 |
| A | Synthetic beeswax | | 0.00 | 5.00 |
| A | Pigments | | 2.65 | 2.65 |
| A | Tricaprylin | | 6.70 | 6.70 |
| A | Pearl | | 4.30 | 4.30 |
| B | Deionized Water | | 30.00 | 30.00 |
| B | b-Polyethyleneimine (50% solid/50% water) | Lupasol G 35 | 0.25 | 0.35 |
| B | Glycerin | | 10.00 | 10.00 |
| | Total | | 100.00 | 100.00 |

The hardness of the sticks in examples 3 and 4 was determined to be 144 and 158 gram-force, respectively.

Procedure:
1. Heated all the oils of phase A in a Beaker 1 at 95° C.
2. Added the Licocare CM401 into beaker 1 containing the oils to dissolve.
3. When the licocare CM401 was totally dissolved, added the wax into beaker 1 and stirred well until wax was dispersed.
4. Added the pigments and pearls into beaker 1 and mixed well.
5. Reduced the temperature of beaker 1 to 85° C.
6. Used the Silverson to mix the phase A content in beaker 1 while maintaining the temperature at 85-90° C.
7. In a separate beaker 2, added the Lupasol G-35 into hot water at 85° C. and stirred well.
8. Added dropwise the Lupasol G-35 solution into the beaker A while the speed of Silversion was increased to 9000 rpm.
9. Left Silverson @ 9000 rpm for 30 minutes, after that reduced speed to 2000 rpm for 5 mins.
10. Poured mixture at 85-90° C. into lipstick molds. Cooled for 20 minutes in refrigerator.

Shine Results:

The shine of examples 2-4 was compared to shine provided by commercially available Maybelline Water Shine product (anhydrous lipstick containing silicone oils). The results were as follows:

| | Lipstick Example 2 | Lipstick Example 3 | Lipstick Example 4 |
|---|---|---|---|
| Immediate Shine | 157.2 +/− 16.9 | 132.4 +/− 23.8 | 130.2 +/− 14.9 |

The shine from the invention lipsticks examples 2-4 was higher or the same as compared to the shine of the commercially available anhydrous lipstick (Maybelline Water Shine=124.5+/−10.0). In addition, the invention lipsticks were very comfort, moist and non-tacky.

What is claimed is:

1. An emulsion lipstick composition, in solid form, comprising:
   (a) water;
   (b) a water-insoluble half acid and half amide crosslinked reaction product of (1) at least one oil-soluble high carbon polar modified polymer comprising at least one C22-C40 monomer and modified with at least one hydrophilic unit, and having a weight-average molecular weight of less than or equal to 30000 g/mol and a crystallinity of 8% to 60% and (2) at least one polyamine, wherein the reaction product forms a matrix capable of entrapping water;
   (c) at least one non-volatile solvent capable of solubilizing the oil-soluble high carbon polar modified polymer; and
   (d) at least on high melting point wax,
   wherein water is entrapped within the matrix.

2. The composition of claim 1, wherein the at least one polyamine is a branched polyethyleneimine.

3. The composition of claim 1, wherein the composition is made using from 0.05 to 5% by weight, based on the weight of the composition, of the polyamine.

4. The composition of claim 1, wherein the composition is made using from 3 to 20% by weight, based on the weight of the composition, of the oil-soluble high carbon polar modified polymer.

5. The composition of claim 1, wherein water is present in an amount of from 0.1 to 50% by weight, based on the weight of the composition.

6. The composition of claim 1, wherein the non-volatile solvent is a non-volatile oil.

7. The composition of claim 1, wherein the non-volatile solvent is present in an amount of from 20 to 90% by weight, based on the weight of the composition.

8. The composition of claim 1, wherein the wax is present in an amount of from 5 to 20% by weight, based on the weight of the composition.

9. The composition of claim, 1 wherein the composition has a hardness value of from about 50 to about 200 gram-force.

10. The composition of claim 1, further comprising at least one colorant.

11. The composition of claim 1, wherein the composition is free of emulsifiers and/or silicone fluids.

12. A method of imparting shine, hydration and/or moisturization onto lips comprising applying onto the lips the composition of claim 1.

13. The composition of claim 1, wherein water is present in an amount of from 5 to 40% by weight, based on the weight of the composition.

14. The composition of claim 1, wherein the oil-soluble high carbon polar modified polymer comprises maleic anhydride groups.

15. The composition of claim 1, wherein the weight-average molecular weight of the oil-soluble high carbon polar modified polymer is from 500 to 10,000 g/mol.

16. The composition of claim 1, wherein the oil-soluble high carbon polar modified polymer comprises at least one C26-C28 monomer.

17. The composition of claim 1, wherein the oil-soluble high carbon polar modified polymer has from about 5% to about 30% hydrophilic units.

18. The composition of claim 14, wherein the oil-soluble high carbon polar modified polymer has from about 5% to about 30% maleic anhydride units.

19. The composition of claim 2, wherein the oil-soluble high carbon polar modified polymer comprises maleic anhydride groups.

20. The composition of claim 2, wherein the weight-average molecular weight of the oil-soluble high carbon polar modified polymer is from 500 to 10,000 g/mol.

21. The composition of claim 2, wherein the oil-soluble high carbon polar modified polymer comprises at least one C26-C28 monomer.

\* \* \* \* \*